United States Patent [19]
Drake et al.

[11] Patent Number: 5,180,379
[45] Date of Patent: Jan. 19, 1993

[54] ELECTRODE WITH PRE-WIRED LEADS

[75] Inventors: Gerald E. Drake, Oakdale, Minn.; Thomas R. Gray, Colon, Nebr.; Paul G. Izen, Inver Grove Heights, Minn.

[73] Assignee: Minnesota Mining and Manufacturing Company, St. Paul, Minn.

[21] Appl. No.: 680,583

[22] Filed: Apr. 4, 1991

[51] Int. Cl.⁵ .................... A61B 17/39; H01R 13/62
[52] U.S. Cl. ........................ 606/32; 128/798; 439/775; 439/790
[58] Field of Search ............... 606/32; 128/639, 640, 128/644, 798, 802; 439/775, 790

[56] References Cited

U.S. PATENT DOCUMENTS

| | | | |
|---|---|---|---|
| 4,061,408 | 12/1977 | Bast et al. | 339/75 R |
| 4,738,263 | 4/1988 | Seebach et al. | 128/640 |
| 4,848,348 | 7/1989 | Craighead | 128/639 |
| 4,848,353 | 7/1989 | Engel | 128/640 |

FOREIGN PATENT DOCUMENTS 3640385  6/1988  Fed. Rep. of Germany ...... 439/790

*Primary Examiner*—Lee S. Cohen
*Attorney, Agent, or Firm*—Gary L. Griswold; Walter N. Kirn; Charles D. Levine

[57] ABSTRACT

An electrode assembly for use in medical applications including an electrode having a conductor, a lead wire, and a connector. The wire is attached to the conductor with the connector. The connector includes two portions which snap together, and one or both portions have a corrugated wire contacting surface. The wire is held in electrical contact with the conductor between the first and second portions of the connector.

14 Claims, 4 Drawing Sheets

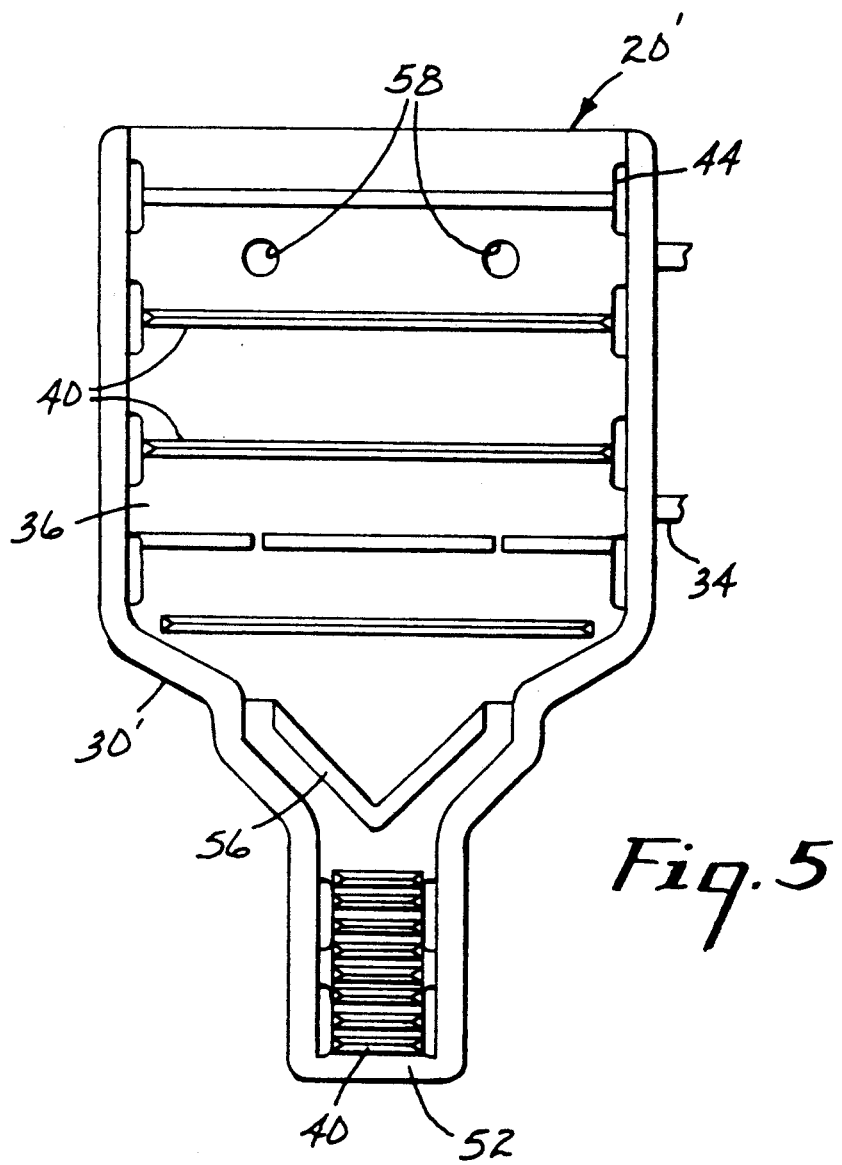

ELECTRODE WITH PRE-WIRED LEADS

TECHNICAL FIELD

The present invention relates to electrical connections. More particularly, the present invention relates to the connection of medical dispersive electrodes to electronic devices, such as permanent lead wires.

BACKGROUND OF THE INVENTION

In many medical diagnostic and therapeutic procedures electrical signals are received by or delivered to a patient's body. The interface between medical equipment used in these procedures and the skin of the patient is usually an electrode. The electrode typically includes a conductor which is connected electrically to the medical equipment by one or more wires. Dispersive electrodes used to return the current used in electrosurgery from the body are typically made with two wires attached to respective tabs projecting from the conductor. With some of these electrodes, two conductors, each having a tab and being attached to a separate wire are adhered to a single backing.

A known method of assembling this class of electrodes involves removing the insulation from the end of the wires, and stapling or riveting the wires to the conductor. The connections are then insulated such as by wrapping foam tape around them. Both of these operations are time consuming and labor intensive, increasing the cost of health care. Additionally, if attachment is not done properly, the assembly must be scrapped.

U.S. Pat. No. 4,738,263 to Seebach et al. discloses a two part connector for providing an electrical connection between an electrode and lead wires. However, these wires are connected to the electrode and the connector with ring terminals which fit over posts on the connector. This increases the cost of parts and labor.

SUMMARY OF THE INVENTION

The present invention overcomes these problems with known systems for connecting electrodes to medical devices. The connector of the present invention connects an electrode having a conductor to one or more wires. The conductor is generally flat. The electrode also has a layer of conductive gel or adhesive contacting one side of the conductor, and has insulation contacting the other side of the conductor. The wires are insulated except at their ends.

The connector has first and second portions, and at least the first portion has a corrugated wire contacting surface. The first and second portions may be two distinct parts, or may be physically joined by a hinge along one edge of each of the portions of the connector. A snap fitting secures the first portion to the second portion. The snap fitting can include a tab attached to one of the first and second portions and a slot attached to the other of the first and second portions wherein the tab and slot complementarily snap together. The wire is held in electrical contact with the conductor between the first and second portions of the connector.

Where the second portion of the connector also has a corrugated wire contacting surface, this surface is preferably complementary to the corrugated wire contacting surface on the first portion. Additionally, a raised ridge may be fabricated on one portion of the connector to prevent the uninsulated portion of the wires in a two wire assembly from contacting each other.

BRIEF DESCRIPTION OF THE DRAWINGS

FIG. 5 is a top view of an alternative embodiment of the connector.

DETAILED DESCRIPTION OF PREFERRED EMBODIMENTS

Figure 1:
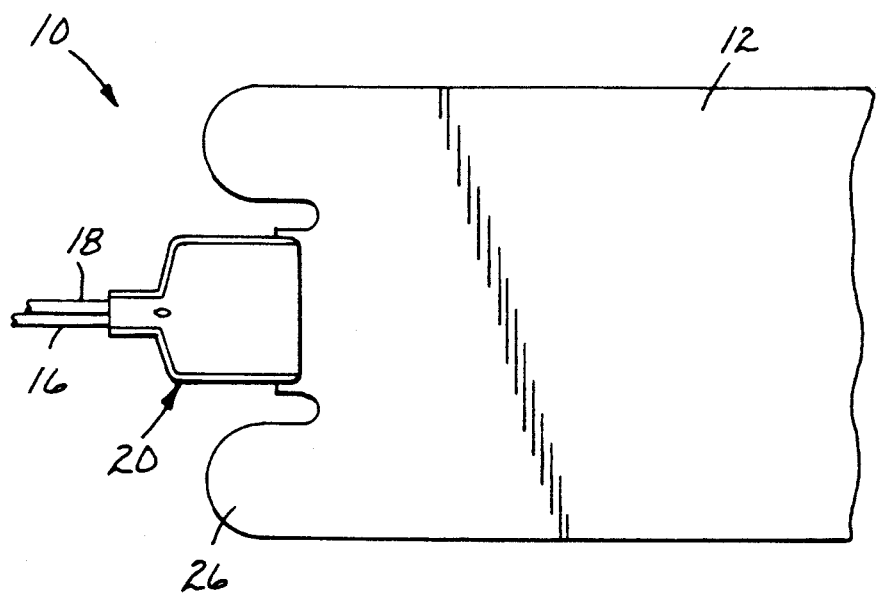
FIG. 1 is an electrode assembly according to the present invention.
Figure 2:
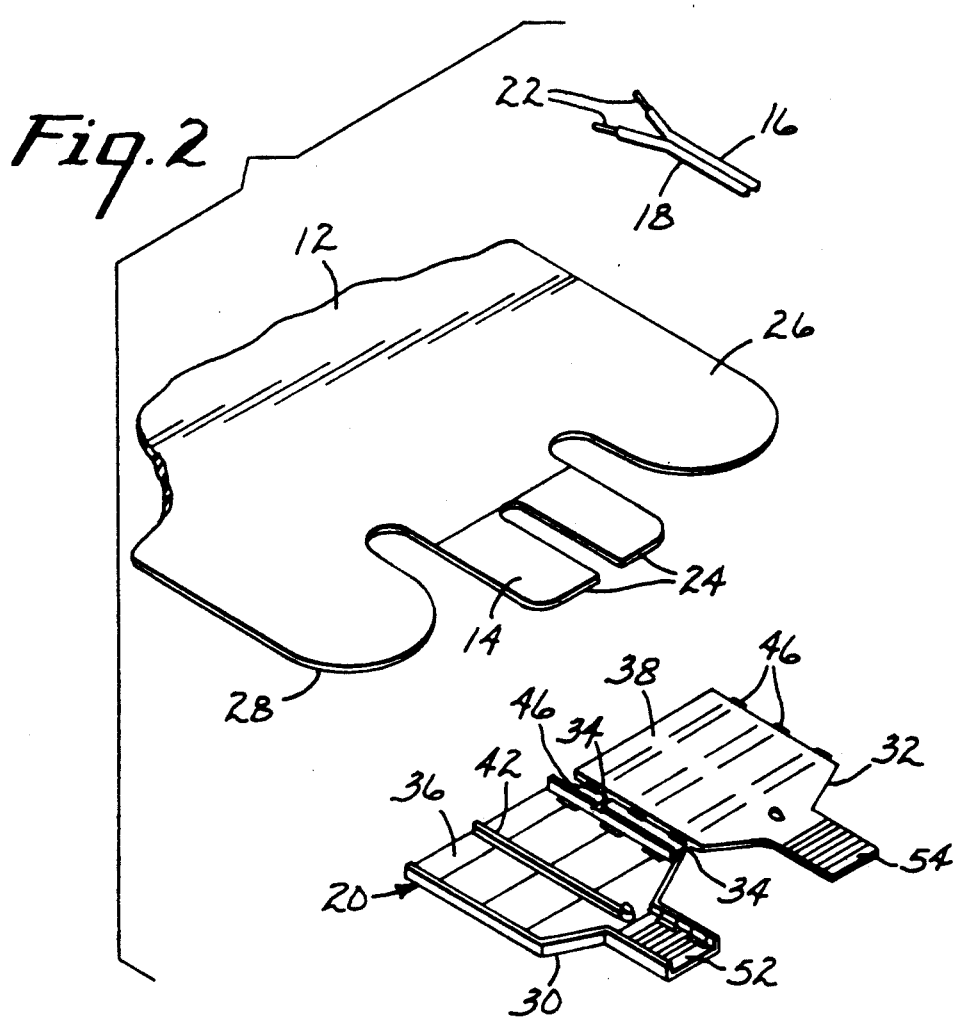
FIG. 2 is an exploded view of the electrode assembly of FIG. 1 prior to assembly.
Figure 3:
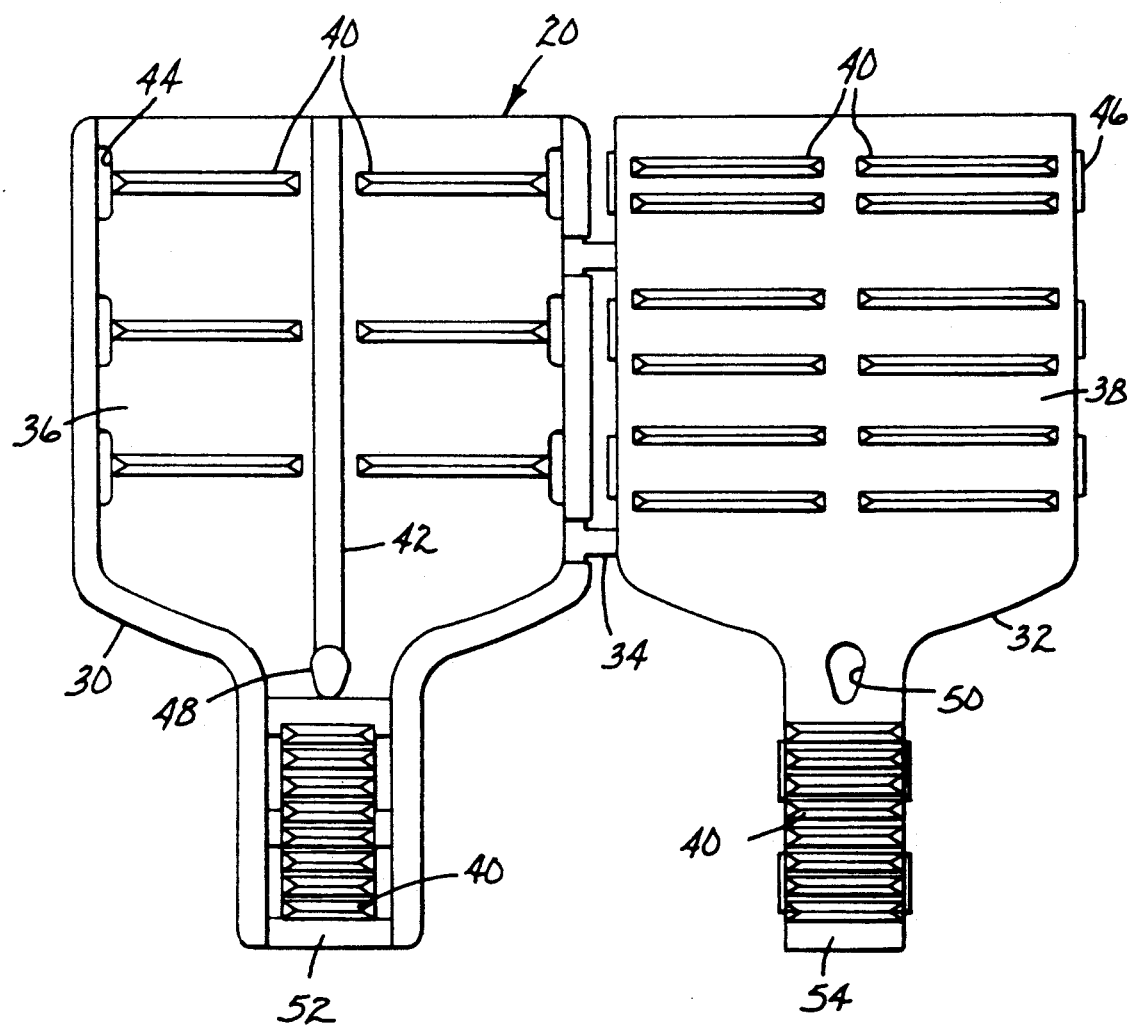
FIG. 3 is a top view of the connector shown in FIG. 2.
Figure 4:
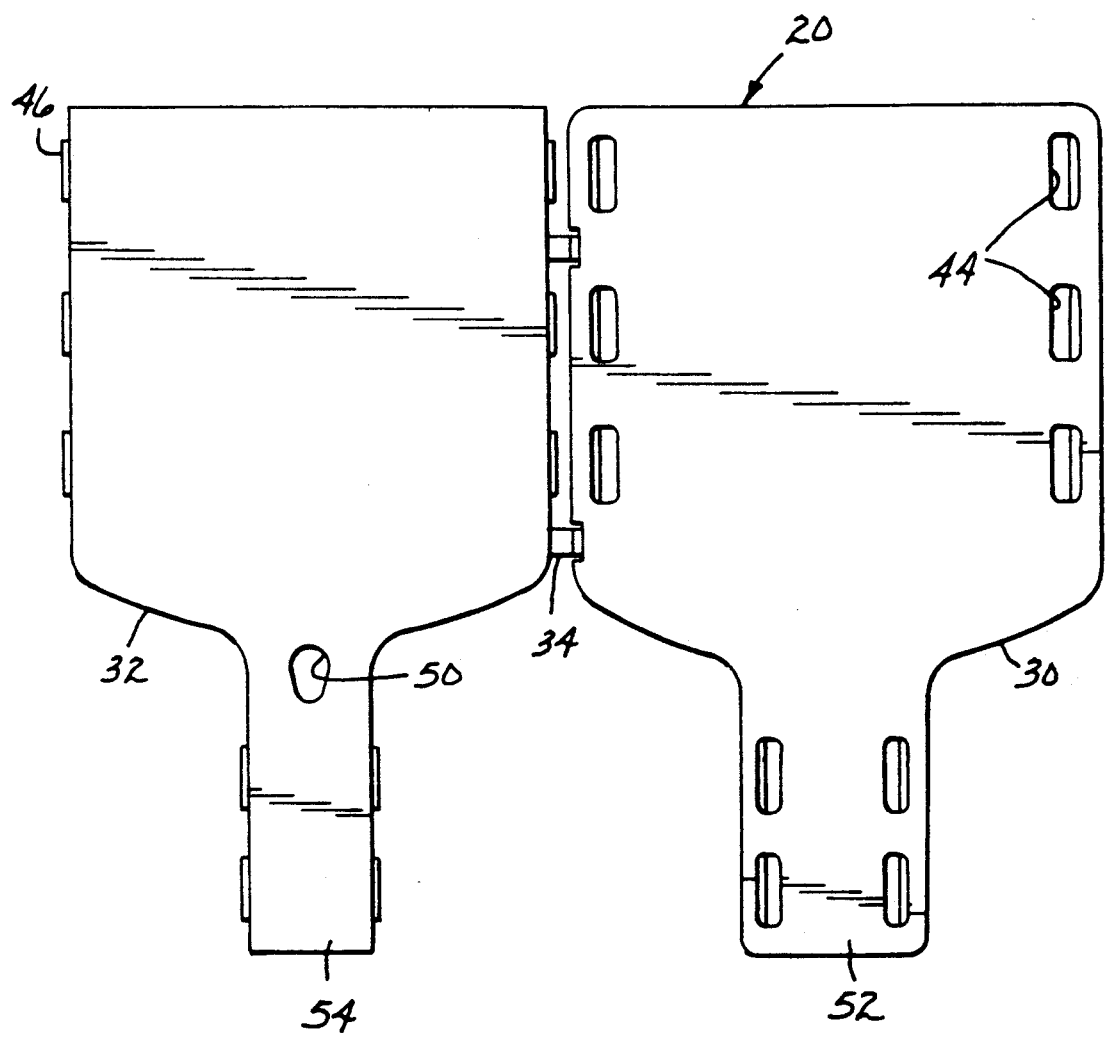
FIG. 4 is an end view of the connector shown in FIG. 2.

The electrode assembly of the present invention connects an electrode and a conductor such as wire using a connector. The electrode assembly is a medical dispersive electrode assembly which serves as the interface between medical equipment and the skin of a patient. In FIG. 1, the electrode assembly 10 is shown assembled. FIGS. 2, 3, and 4 illustrate the details of the electrode assembly 10 prior to assembly. The electrode assembly 10 includes an electrode 12 having a conductor 14 and connected to one or more wires 16, 18 by a connector 20. The conductor 14 is generally flat, and may be made of metal (e.g. aluminum or tin), or may be made of a polymeric sheet having a conductive coating. The making of an exemplary coating is discussed in coassigned U.S. Pat. No. 4,848,348 to Craighead, which is incorporated herein by reference.

As shown, there are two wires, 16, 18, both of which terminate in two uninsulated ends 22. The conductor 14 of the electrode 12 is exposed along two tabs 24. Except for the tabs 24, one side of the conductor 14 is covered by an insulative backing 26 and the other side of the conductor 14 is covered by a layer of conductive adhesive 28 or conductive gel for contact with the patient's skin. In preferred embodiments of the electrode assembly 10 the backing 26 extends laterally beyond the conductor 14 to protect the outside edge of the conductive adhesive 28. A skin adhesive may be used on the underside of the backing 26 generally surrounding the conductive adhesive 28 to improve the adhesion of the electrode assembly 10 to the surface of the skin. A discussion of conductive adhesives and their use in medical electrodes can be found in coassigned U.S. Pat. No. 4,848,353 to Engel, which is incorporated herein by reference. The connector 20 preferably is fabricated from a polymeric material, such as polycarbonate or polypropylene. Preferred methods of fabrication include machining and preferably injection molding.

The connector 20 includes a first portion 30 and a second portion 32. The first and second portions 30, 32 may be fabricated in two distinct parts, or may be physically connected along one edge by a hinge 34. The first portion 30 has a first wire contacting surface 36 and the second portion 32 has a second wire contacing surface 38. Both the first and second wire contacting surfaces 36, 38 are textured although in alternative embodiments only one surface could be textured. Preferably the texture includes corrugations 40 and the corrugated surfaces 36, 38 are complementary. The corrugated surfaces 36, 38 are adapted to grip the uninsulated ends 22 of the wires 16, 18 against the tabs 24 when the electrode assembly 10 is assembled. The corrugated surfaces 36, 38 provide sufficient gripping force to create good conductivity between the wires 16, 18 and the conductor 14 and enable the connector 20 to withstand the required 89 N (20 lb) of pullout force.

A raised ridge 42 may be fabricated on or attached to the first portion 30 of the connector 20 to prevent the uninsulated ends 22 of the wires 16, 18 in a two wire assembly from contacting each other.

The connector 20 is secured around the wires 16, 18 and the conductor 14 by placing the uninsulated ends 22 of the wires 16, 18 against the tabs 24 of the conductor 14. The connector 20 is closed by pivoting the two portions 30, 32 of the connector 20 relative to each other by bending the hinge 34 so that the wire contacting surfaces 36 and 38 face each other and hold the wires 16, 18 in between. Several snap fittings secure the two portions 30, 32 together. The snap fittings include female slots 44 formed on the first portion 30 and male tabs 46 formed on the second portion 32. The tabs 46 may include lips which hook through the slots 44. The snap fittings may be openable or permanently closed. Alternatively, various other latching arrangements can be used to connect the first and second portions 30, 32 of the connector 20.

In FIG. 3, the complementary pattern of the corrugations are shown. Additionally, a projection 48 on the first portion 30 is adapted to engage an opening 50 on the second portion 32 when the portions are opposed to facilitate proper alignment during assembly and to assist the raised ridge 42 in separating the wires 16, 18. Optionally, the connector 20 may have first and second necks 52, 54 on the first and second portions 30, 32, respectively, for supporting and gripping the insulated part of the wires 16, 18. The necks 52, 54 may have corrugations 40 of their own to facilitate this function, and snap fittings may be used on the necks 52, 54.

In an alternative embodiment shown in FIG. 5, the first portion 30' of the connector 20' is shown. The straight raised ridge 42 is replaced with a V-shaped raised ridge 56 which directs the wires 16, 18 to their respective sides of the connector 20'. Additionally, test probe openings 58 are formed in the first portion 30' to receive test probes which measure conductivity to determine whether the wires 16, 18 are properly located.

The connector holds an otherwise unprepared lead wire against the conductor of the electrode. There is no need to secure a ring or other specialty terminals to the wires by crimping or otherwise and the wires need not be specially prepared. Also, as the connector can be snapped over the electrode tabs and the wires by hand or with a press, assembly is simpler and cheaper than using staples or rivets. Nor is any additional insulation required as the connector serves as an insulator. Additionally, unlike stapled or riveted assemblies, if mistakes or errors occur during fabrication or assembly, the connector can be disassembled and the damaged component is replaced or the fault is corrected, thereby reducing waste.

Numerous characteristics, advantages, and embodiments of the invention have been described in detail in the foregoing description with reference to the accompanying drawings. However, the disclosure is illustrative only and the invention is not intended to be limited to the precise embodiments illustrated. Various changes and modifications may be effected therein by one skilled in the art without departing from the scope or spirit of the invention.

We claim:

1. A connector for a medical dispersive electrode assembly wherein the electrode assembly serves as the interface between medical equipment and the skin of a patient and includes an electrode having a conductor and at least one wire, the connector comprising:
    a first portion;
    a second portion;
    means for securing the first portion of the connector to the second portion of the connector with the wire and conductor therebetween; and
    means for holding the wire in electrical contact with the conductor between the first and second portions of the connector, wherein the holding means is separate from the securing means and includes a textured wire contacting surface mounted on the first portion of the connector.

2. The connector of claim 1 wherein the textured wire contacting surface is corrugated and the second portion of the connector has a corrugated wire contacting surface which is complementary to the corrugated wire contacting surface on the first portion of the connector.

3. The connector of claim 1 wherein the electrode assembly comprises two wires each of which has an uninsulated portion, and the connector further comprises a raised ridge attached to the first portion of the connector to prevent the uninsulated portions of the wires from contacting each other.

4. The connector of claim 3 wherein the raised ridge is V-shaped.

5. The connector of claim 1 wherein the first and second portions of the connector have opposing first and second edges, wherein the first and second portions are hingedly connected together along the first edges and wherein the first and second portions are connected together along the second edges.

6. The connector of claim 1 wherein the securing means comprises a tab attached to one of the first and second portions and a slot attached to the other of the first and second portions wherein the tab and slot complementarily snap together.

7. The connector of claim 1 wherein the electrode assembly comprises two wires and wherein the first portion of the connector comprises means for determining whether the wires are properly located within the connector after the first and second portions of the connector are secured together.

8. The connector of claim 7 wherein the determining means includes openings which receive test probes.

9. A medical dispersive electrode assembly wherein the electrode assembly serves as the interface between medical equipment and the skin of a patient and includes an electrode having a conductor and at least one wire, the assembly comprising:
    an electrode having a conductor;
    at least one wire;
    a connector having first and second portions;
    means for securing the first portion of the connector to the second portion of the connector with the wire and conductor therebetween; and
    means for holding the wire in electrical contact with the conductor between the first and second portions of the connector, wherein the holding means is separate from the securing means and includes a textured wire contacting surface mounted on the first portion of the connector.

10. The electrode assembly of claim 9 wherein the textured wire contacting surface is corrugated and the second portion of the connector has a corrugated wire contacting surface which is complementary to the corrugated wire contacting surface on the first portion of the connector.

11. The electrode assembly of claim 9 wherein the electrode assembly comprises two wires each of which has an uninsulated portion, and the connector further comprises a raised ridge attached to the first portion of the connector to prevent the uninsulated portions of the wires from contacting each other.

12. The electrode assembly of claim 9 wherein the first and second portions of the connector have opposing first and second edges, wherein the first and second portions are hingedly connected together along the first edges and wherein the first and second portions are connected together along the second edges.

13. The electrode assembly of claim 9 wherein the securing means comprises a tab attached to one of the first and second portions and a slot attached to the other of the first and second portions wherein the tab and slot complementarily snap together.

14. The electrode assembly of claim 9 wherein the electrode assembly comprises two wires and wherein the first portion of the connector comprises means for determining whether the wires are properly located within the connector after the first and second portions of the connector are secured together, wherein the determining means includes openings which receive test probes.

* * * * *